United States Patent
Kerr et al.

(10) Patent No.: US 6,625,515 B2
(45) Date of Patent: Sep. 23, 2003

(54) ROLL DEFECT MANAGEMENT PROCESS

(75) Inventors: Tedd Kerr, Stoney Creek (CA); Ron Webber, Ancaster (CA); Ron Howard, Brantford (CA); William Hill, Dundas (CA)

(73) Assignee: Dofasco Inc., Hamilton (CA)

( * ) Notice: Subject to any disclaimer, the term of this patent is extended or adjusted under 35 U.S.C. 154(b) by 224 days.

(21) Appl. No.: 09/741,192

(22) Filed: Dec. 21, 2000

(65) Prior Publication Data

US 2002/0116980 A1 Aug. 29, 2002

(51) Int. Cl.⁷ ............................................... G01N 27/82
(52) U.S. Cl. ..................... 700/148; 700/145; 700/150; 700/164; 73/602
(58) Field of Search ............................... 700/148, 164; 73/602, 620, 622, 643

(56) References Cited

U.S. PATENT DOCUMENTS

| | | |
|---|---|---|
| 3,332,278 A | 7/1967 | Wood et al. |
| 3,939,404 A | 2/1976 | Tait |
| 4,445,089 A | 4/1984 | Harrison |
| 4,495,587 A * | 1/1985 | Plante et al. ................. 702/38 |
| 4,755,753 A * | 7/1988 | Chern ......................... 324/237 |
| 4,924,182 A * | 5/1990 | Vernon et al. .............. 324/237 |
| 5,010,494 A * | 4/1991 | Lord ........................... 702/35 |
| 5,047,719 A * | 9/1991 | Johnson et al. ............. 324/242 |
| 5,392,652 A * | 2/1995 | Levesque et al. ............. 73/629 |
| 5,430,376 A * | 7/1995 | Viertl ......................... 324/227 |
| 5,469,743 A * | 11/1995 | Zorn ............................ 73/627 |
| 5,474,225 A * | 12/1995 | Geier et al. ................. 228/104 |
| 5,481,916 A * | 1/1996 | Macecek et al. .............. 73/601 |
| 5,763,786 A | 6/1998 | Camplin et al. |
| 5,894,092 A * | 4/1999 | Lindgren et al. ............. 73/598 |
| 5,963,918 A * | 10/1999 | Reagan et al. ................ 705/28 |
| 6,184,924 B1 * | 2/2001 | Schneider et al. ............ 348/92 |

OTHER PUBLICATIONS

"Eddy Current Inspection Of Sendzimir Mill Work Rolls and a Computerized Roll Management System"—Wallace J Klein, 1990.*

Eddy Current Inspection of Sendzimir Mill Work Rolls and a Computerized Roll Management System, 1990 Mechanical Working and Steel Processing Proceedings, Wallace J. Klein.

High Speed Steel Roll Trials & Performance at Dofasco, Kerr E.J., 36th MWSP Conf Proc, ISS–AIME, vol. XXXII, 1995 p. 37.

Tool Steel Work Roll Maintenance at Dofasco, Hill W. & Kerr E., 37th MWSP Conf Proc, ISS–AIME, vol. XXXIII, 1996 p. 283.

The Performance of High Speed Steel Rolls at Dofasco, Webber Ron, 37th MWSP Conf Proc, ISS–AIME, vol. XXXIII, 1996 p. 267.

(List continued on next page.)

*Primary Examiner*—Leo Picard
*Assistant Examiner*—Michael D. Masinick
(74) *Attorney, Agent, or Firm*—Ingrid E. Schmidt

(57) ABSTRACT

The Roll Defect Management Process (RDMP) is a system which is designed to manage, track and evaluate all mill rolls found in use in the hot and cold production of flat rolled metal strip. The RDMP is capable of detection, distinction and differentiation of various defects found in the mill roll using a nondestructive inspection system for generating variable amplitude output voltage signals corresponding to changes in physical properties found in a mill roll and defines corrective action for each roll type, mill, stand and position. The disposition and corrective actions of the RDMP are automated and dependent on the determination of various thresholds identified by roll, mill and stand.

30 Claims, 10 Drawing Sheets

OTHER PUBLICATIONS

Evaluation of the Coefficient of Friction for HSS Rolls from Hot Strip Mill Log Book Data, Munther Per A., Webber Ron and Lenard J.G., 37th MWSP Conf Proc, ISS–AIME, vol. XXXIII, 1996 p. 39 and Reprinted in Steel World vol 4 No. 2 P36.

The Use of High Speed Steel Rolls in the Hot Mill Finishing Stands at Dofasco, R.J. Webber, E.J. Kerr and W. Hill, The Institute of Materials Rolls 2000 Conference, Birmingham UK, Mar. 1996.

High Speed Steel Work Rolls at Dofasco's Hot Mill, E.J. Kerr, R.J. Kerr, R.J. Webber and W. Hill, The Institute of Materials Rolls 2000+ Conference, Birmingham UK, Mar. 1999.

High Speed Steel Work Rolls at Dofasco, Edward J. Kerr, 41st MWSP Conf Proc, ISS–AIME, vol XXXVII 1999 p. 117.

The Use of CPC Rolls at Dofasco, R.J. Webber 41st MWSP Conf Proc, ISS–AIME, vol XXXVII, Oct. 1999 p. 579.

* cited by examiner

ROLL DEFECT MANAGEMENT PROCESS

BACKGROUND TO THE INVENTION

1. Field of the Invention

This invention relates to a method of inspecting, testing, evaluating and repairing mill rolls used for flat rolled metal strip production in order to maximize the quality, production and cost efficiency potential of various types of rolls used in rolling flat strip products by detection, differentiation (classification) and correct application of methods for elimination of various defects found in mill rolls.

2. Background Information

Flat rolled strip production employs various types of steel and cast iron work rolls and backup rolls to reduce the thickness of steel slabs to the desired finished product thickness and width of flat rolled strip in coil form. The reduction in thickness employs high forces in both hot mills and cold rolling mills to elongate the steel bar and strip while delivering the desired physical and metallurgical properties to the strip product.

Flat rolling employs both continuous and semi-continuous rolling processes in hot mills and cold mills. Of critical importance is the thickness control, the shape and flatness, and the surface condition of the flat rolled strip. Variations in quality of these factors can result in processing cost increases, extra maintenance of equipment, production losses, and late deliveries of products to both downstream internal customers and external customers.

Various types of rolls are used in flat rolling, including cast iron, cast steel, high chrome iron, forged steel, tool steel and high speed steel. Rolls come in various sizes depending on the mill design ranging from 75 mm diameter to 2000 mm diameter and with a body length ranging from 1000 mm to 2500 mm. Rolls are commonly made from a variety of processes including: static casting, centrifugal spin casting, electro slag re-melt casting and continuous pour clad casting.

Roll performance is commonly evaluated by measurements including: total tonnage rolled, tonnage rolled per campaign, tonnage rolled per inch or mm of roll consumption, or specific roll force (force per unit width). Roll performance is affected by mill operation, rolling schedule, mill equipment condition, practices and procedures, product type and chemistry, roll inspection methods, roll maintenance procedures, roll use practices and roll inventory.

Rolls are highly susceptible to damage from a variety of failure modes, including: spalling, breakage, cracking, fatigue, wear, surface roughening, impression marks, bruising, hardness variation, or expression marks. Detection of defects is critical. However, current state of the art systems fail to allow differentiation of various types of cracks and the application of appropriate measures for the treatment of these cracks.

Various inventions about automatic inspection and testing of mill rolls have described ways and means for the use of eddy currents, ultrasonic sound and/or electro-magnetics to check the surface and interior of mill rolls normally used in the production of flat rolled steel strip and other flat rolled metallic products. Such inventions are described in U.S. Pat. Nos. 5,763,786; 4,495,587; and 3,939,404. To date, mill roll grinders and lathes use Computerized Numerical Control (CNC) programs to execute standard programs to repair and maintain the rolls. It is common for these programs to be supplied by the machine manufacturer and in many cases, it is difficult and time consuming to change the programs. These generic programs waste time and cause excessive material to be removed from the mill roll. Also, incorrect logic is used for new roll technology due to the lack of expert roll related knowledge available to the machine manufacturer. An improved method of controlling machine action will result in significant savings in metal consumption, machine and operator time and mill performance results. In addition, improved control will allow failure risk levels to be more carefully managed. Grind programs at the CNC level must be suitable to many various roll types. The program should react to many diverse inputs and accommodate changes as demanded by the quality level of the product being manufactured.

SUMMARY OF THE INVENTION

The invention provides a method for inspecting a mill roll used for producing flat rolled metal strip and for disposition of a mill roll of predetermined type and in service on a predetermined mill stand as a function of any defects detected in said mill roll, the method comprising the steps of:

a) applying a nondestructive inspection system to generate variable amplitude output voltage signals corresponding to changes in physical properties along a reference direction for at least a portion of the mill roll, any said changes in physical properties corresponding to a mill roll defect;

b) defining an output voltage signal pattern from said variable amplitude output voltage signals;

c) classifying said mill roll defect in accordance with predetermined patterns of output voltage signals;

d) selecting a threshold signal value corresponding to said classified mill roll defect for the type of mill roll being inspected on said mill stand;

e) calculating a difference between a maximum peak height for the output voltage signals and said threshold signal value; and f) defining corrective action for disposition of the mill roll in accordance with said calculated difference.

The invention allows automatic decision making for roll maintenance practices to be employed in order to attain the highest performance possible, without incurring risk of roll failure and without incurring risk of lost mill operating time or quality defects when using said work rolls or backup rolls.

The invention also provides a system for inspecting mill rolls used in the production of flat rolled metal strip and for defining corrective action for disposition of mill rolls, the system comprising:

a) data input means for receiving data defining a roll history and mill history associated with a roll being inspected;

b) a database of threshold signal values each corresponding to an acceptable output voltage signal for a roll having a predetermined roll history and mill history and having a predetermined type of mill roll defect;

c) a nondestructive inspection system for generating variable amplitude output voltage signals corresponding to changes in physical properties associated with mill roll defects;

d) signal processing means for receiving said variable amplitude output voltage signals and defining a voltage signal pattern;

e) signal classification means for classifying said voltage signal pattern in accordance with predetermined patterns of output voltage signals associated with predetermined types of mill roll defects each having a predetermined threshold signal value;

f) computation means to calculate a difference in a maximum peak height between the output voltage signals characterizing said voltage signal pattern and said predetermined threshold signal value and to define corrective action for disposition of the mill roll; and g) transfer means for conveying information about said corrective action.

Various roll grinder process measurements are taken automatically by a Grinder CNC Control Program, including caliper measurements of the roll diameter, roll temperature, shape, runout and eccentricity. Data values are transferred automatically to a database and stored. The CNC control system also displays values in chart output format on a CRT (cathode ray tube) display. An automatic grind program selection module in the computer control system chooses the correct CNC grind program to achieve the optimum target grind level for the specified roll type, mill stand and rolling schedule type.

Grind program selection logic is developed offline and is based on roll performance management strategies developed in the operating plant. Key functions include the target grind levels for each roll type, the tolerance levels and risk levels permitted by the rolling operation, and the optimum use strategy employed at the rolling operation.

In addition to grinder process measurements, automatic eddy current and ultrasonic testing equipment measurements are transferred automatically to a database and stored. The database also contains a table of threshold values for each roll type, mill stand, and rolling schedule. A second computer module compares the output values of the grinding process and the output values of the eddy current and ultrasonic test equipment to the threshold values and an automatic decision is made to return to a grind program selection module or to enter a finish grind program module.

A third computer module evaluates the output values of the eddy current and ultrasonic systems and through a process of logical steps classifies the various defect types which may exist within the roll surface, shell or core. These classified types, along with their severity ratings are passed to the threshold comparison module that then allows the correct grind program selection to take place.

The ability to automatically detect defects within the roll surface, shell and core using automatic detection equipment is valuable information. Utilizing the automatic defect recognition software elevates the value of such information considerably. A model predicts the defect type based on statistical information and standard values that have been established by review and study of many and various types of rolls. Standard values are developed by resident experts in roll technology, roll testing and process experts off line.

Threshold values are established offline based on many roll condition observations in the operating plant and are formulated into a useful table. The collection and organization of these threshold values is the key to the ability of the grind program selection module to function for performance optimization.

A graphical tabulation of threshold signal values is provided, the threshold signal values each corresponding to an acceptable output voltage signal for a roll having a predetermined roll history and mill history and having a predetermined type of mill roll defect. The threshold signal values are preferably displayed as a bar chart with the height of a bar associated with a first axis corresponding to output voltage signals generated by a nondestructive inspection system and a second axis corresponding to a depth of material to be removed from a mill roll.

In accordance with another aspect of the invention, a roll mill insert comprising a plate for mounting on a mill roll is provided, the plate having defects formed therein for generating output voltage signals of predetermined amplitude to calibrate a nondestructive inspection system.

DESCRIPTION OF FIGURES AND DRAWINGS

FIG. 5(*b*) is a schematic representation of a photomicrograph showing a stress induced crack propagation to the interior of a roll;

DETAILED DESCRIPTION OF THE PREFERRED EMBODIMENT

Figure 1:
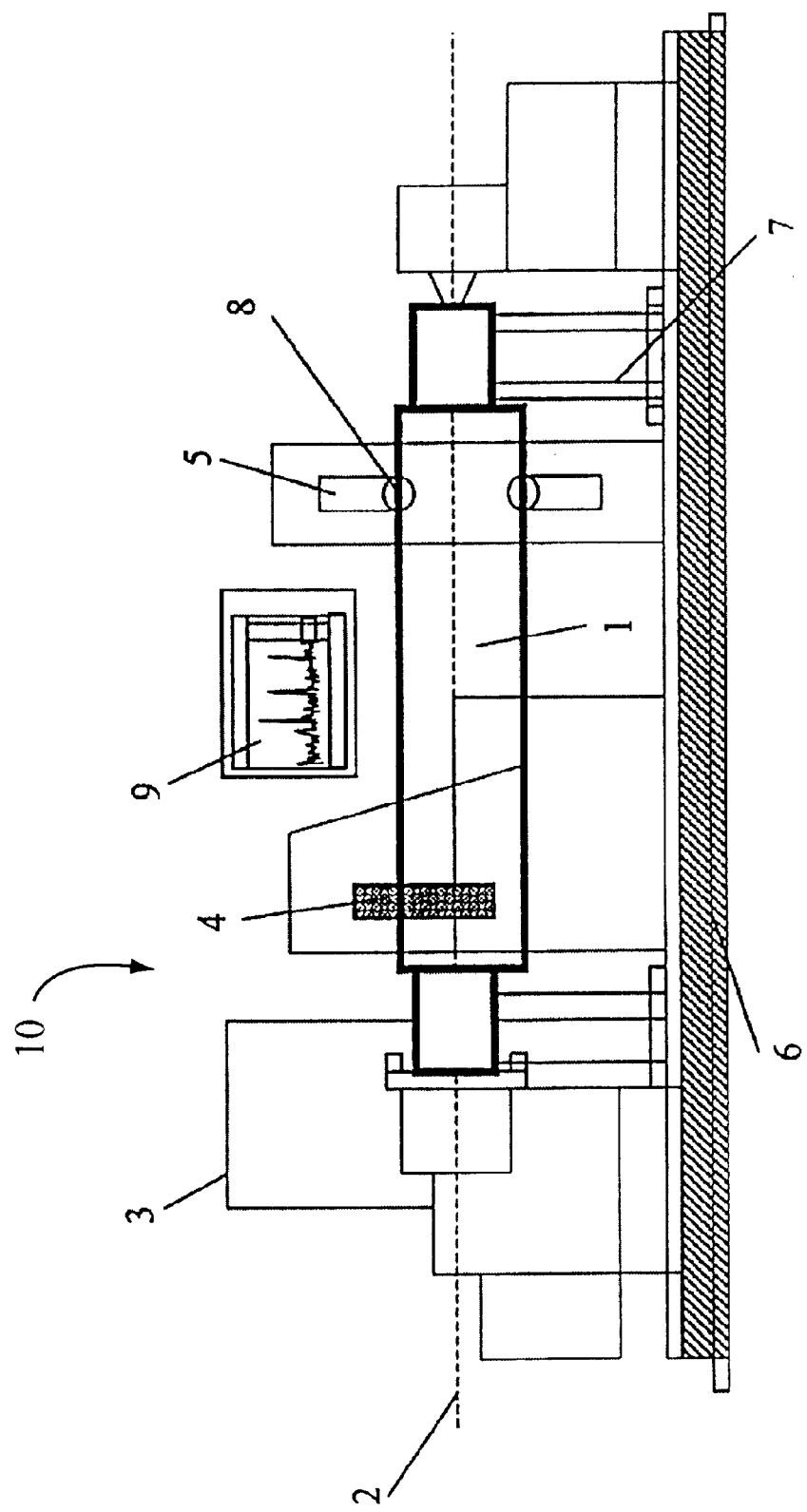
FIG. 1 is a schematic side elevation showing a roll grinding machine for treatment of mill rolls in the metalworking industry.

Mill rolls for use in the metalworking industries are used to produce flat rolled and shaped metal products. Mill rolls come in a variety of sizes and shapes according to the product being made and are useful for continuous operations for various lengths of time. Periodically, they are removed from service and maintained using a roll grinding machine generally indicated in FIG. 1 by reference numeral 10. The roll grinding machine 10 is used to return the rolls to their specified condition, and remove any surface defects after inspecting the rolls for damage. The roll grinding machine 10 accommodates a roll 1, which is driven by motors on a horizontal axis 2. The grinding machine 10 is normally controlled by a manual or automatic system 3 that powers and manipulates a grinding wheel 4 that is used to remove material from the roll. The grinding machine is mounted on a steel base 6 while the roll 1 is supported on steady rests 7. A system of calipers and test heads (5,8) is used to measure the diameter of the roll along its axis and to test the surface and interior of the roll for cracks and other types of defects commonly found in mill rolls. The results of the inspection are generally displayed on a computer screen, chart recorder or via a number of indicator lights 9.

Figure 2:
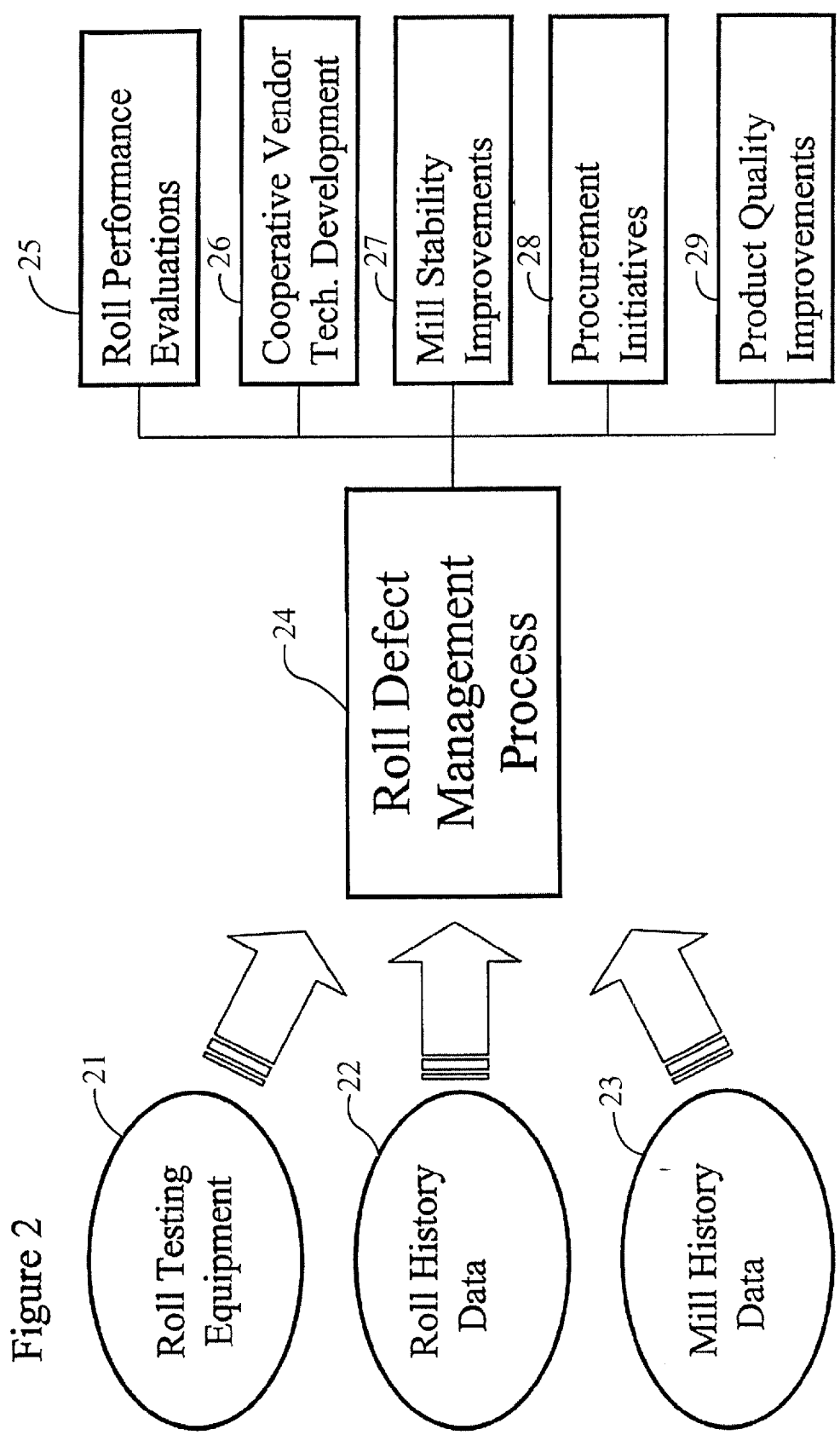
FIG. 2 is a flowchart showing various inputs to a Roll Defect Management Process in accordance with the invention and associated benefits.

The benefits of a comprehensive Roll Defect Management Process 24 in accordance with the invention are outlined in FIG. 2. With various inputs provided by Roll Testing Equipment 21 (including eddy current testing or ultrasonic testing), Roll History Data 22 (from various types and kinds of databases), and Mill History Data 23 (including mill control systems, computers and databases), the Roll Defect Management Process 24 provides benefits as noted, including thorough and detailed roll performance evaluations 25, cooperative vendor technology development 26, improvements in mill equipment and operation resulting in a more stable operations 27, assessment of various procurement initiatives 28, and most important—the improvement of the finished product quality 29. All of these benefits lead to significant cost savings for the operation.

As mill rolls are the chief tool in the operation of rolling mills, their use is subject to many effects. During its service life (which can span a few months or up to many years), a mill roll is exposed to high stress, heat, impacts and other causes which damage the rolls and which cause strip marks and other defects which adversely affect the quality of the flat rolled metal strip product. In addition, a variety of defects may be present in the roll inherent to the manufacturing process. These may not be detected until the useful shell of the roll has been partially consumed. These defects include: cracks, voids, indentations, variations in microstructure, inclusions, and variations in hardness. Various nondestructive inspection systems are employed to detect the presence of such defects, including eddy current and ultrasonic methods.

Eddy currents induced in a roll react to changes in physical properties such as changes in the electrical conductivity of the material and test parameters in the area under the probes. Filtering and auto-zero circuits reduce the non-defect responses such as gap variances and temperature. Ultrasound waves react to changes in the acoustic impedance of the usable shell material of a roll and the bond region of composite roll.

Figure 3:
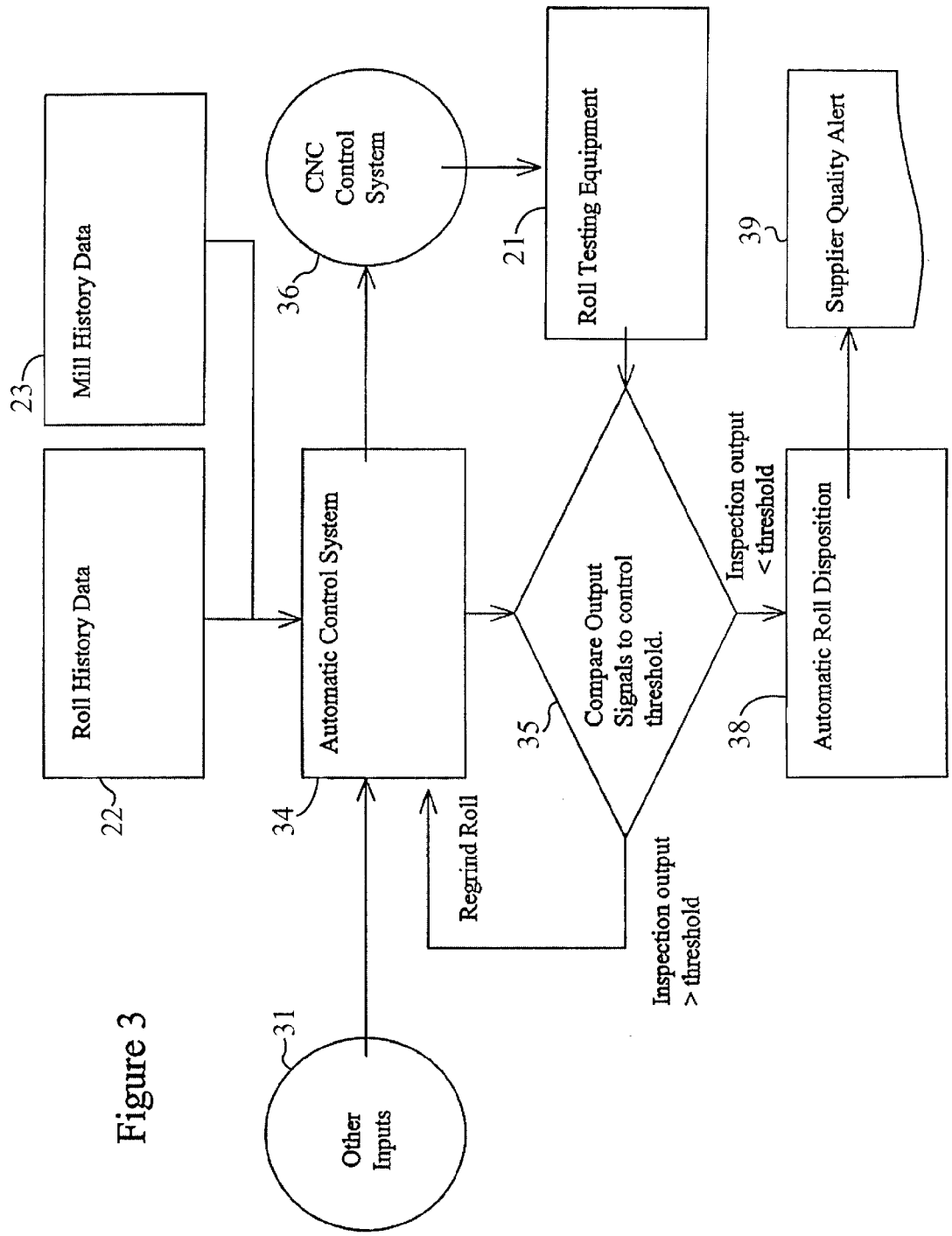
FIG. 3 is a flowchart showing a system for implementing the Roll Defect Management Process in accordance with the invention.

FIG. 3 demonstrates a system by which various inputs are used in the Roll Defect Management Process 24 of FIG. 2. Roll History Data identified by area 22 will include information about a mill roll such as an identification tag and the size of the roll, shape, runout and eccentricity, the material of construction, whether iron or high speed steel, for example, and the construction type, for example whether it is a composite layered roll or uniform.

Mill History Data identified by area 23 will include information about rolling mill operations associated with a roll having a predefined identification tag such as the mill stand where the roll was used in current and previous campaigns, the mill operating temperature, a mill output product tag such as the material, width, and gauge of flat rolled metal strip being produced in the current campaign and previous campaigns, and any other data about the mill operations such as incident reports noting for example that strip was held stationary between rolls possibly causing some localized overheating in the case of a hot rolling operation. To the extent that such other data may be collected by manual and visual inspection conducted by operators and is not automated, such inputs are identified separately in FIG. 3 by area 31. These inputs 22, 23, 31 are used to allow an automatic selection of grinding machine parameters in an Automatic Control System 34. These parameters include setpoints, speeds, feedrates, actions, movements; in short-all aspects of the machine control system. This selection is targeted to the specific mill stand, roll type, and rolling condition, including target quality level and/or specification. The selection is subsequently output to a computerized numeric control system (CNC) 36, where the specific steps in the grind activities are initiated and controlled. These steps include number of rough passes, number of finish passes, and crown/taper/finish passes.

Roll Testing Equipment 21 consisting of eddy current and/or ultrasonic testing provide additional input data to the selection of grinding machine perameters in the Automatic Control System 34. Variable amplitude output voltage signals generated from eddy current or ultrasonic inspection systems are compared to threshold values and if the comparisons 35 yield positive results, the roll can be dispositioned for use 38. If the comparisons yield negative results, the roll must be reground and a new grind program is selected in the Automatic Control System 34. Various disposition results are possible, including a supply quality alert which may be automatically generated 39 where it is determined that the roll has an inherent manufacturing defect and must be returned to a supplier.

Before a comparison to threshold values can be made, the nature of a defect in a mill roll must be classified. In general, the defects which occur in a mill roll may be attributed to localized heating for hot rolling operations or to mechanical impacts or to a combination of these, in additional to any inherent construction or material defects, or defects caused by improper grinding of the rolls.

The localized heat effect from a hot metal strip contacting a roll during an unscheduled stoppage in a mill will generate thermal cracks in the contact area. Such thermal cracks are identified by reference numeral 42 in the photomicrograph of FIG. 4. On the roll surface their appearance is similar to a net and parallel to the centerline. Their internal crack propagation is perpendicular to the surface as indicated by reference numeral 51 in the photomicrograph of FIG. 5(*a*). The length of the crack network is determined by the width of the metal strip product. Thermal cracks are typically longer and more open to the surface than pressure cracks. Continued use of rolls containing thermal cracks can lead to spalls and pitting.

Pressure cracks are generated by local overstressing of the roll material. Excessive pressure during rolling can be caused by folds in the strip and incorrect roll chamfers. These cracks propagate into the roll at angles of approximately 45 degrees as indicated by reference numeral 52 in the photomicrograph of FIG. 5(*b*). Impacts can also cause internal cracks below the surface and separation of the interface(s) in composite rolls. Continued use of rolls with pressure cracks can lead to catastrophic roll failures.

Metallurgical anomalies from the manufacturer can occur randomly throughout the usable material on the roll including any interfaces. They can be any size. A nondestructive surface inspection technique will indicate changes in hardness due to improper heat treatment or thin shell exposure prior to the normal roll scrap diameter. Grinding defects may be generated due to improper procedures and machine faults.

Pattern Recognition

The Roll Testing Equipment 21 (FIG. 2) is normally carried on an inspection transport system incorporated into a grinder carriage forming part of the roll grinding machine 10 (FIG. 1) to ensure 100% coverage of a roll surface while maintaining a constant probe/roll gap and roll rotational speed as the inspection system moves along the roll axis. Grinder operators can with proper training and experience differentiate thermal cracks from pressure cracks by visually inspecting an output voltage signal pattern of any defect locations and comparing the pattern to known defect patterns. The locations are referenced to the key way position on a roll neck.

Figure 4:
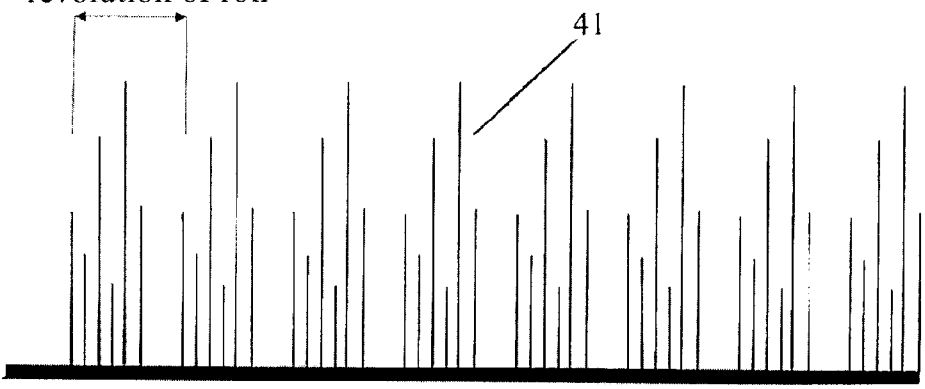
FIG. 4 is a schematic representation of a photomicrograph and associated eddy current voltage plot showing a typical thermal crack at the roll surface.
Figure 4:
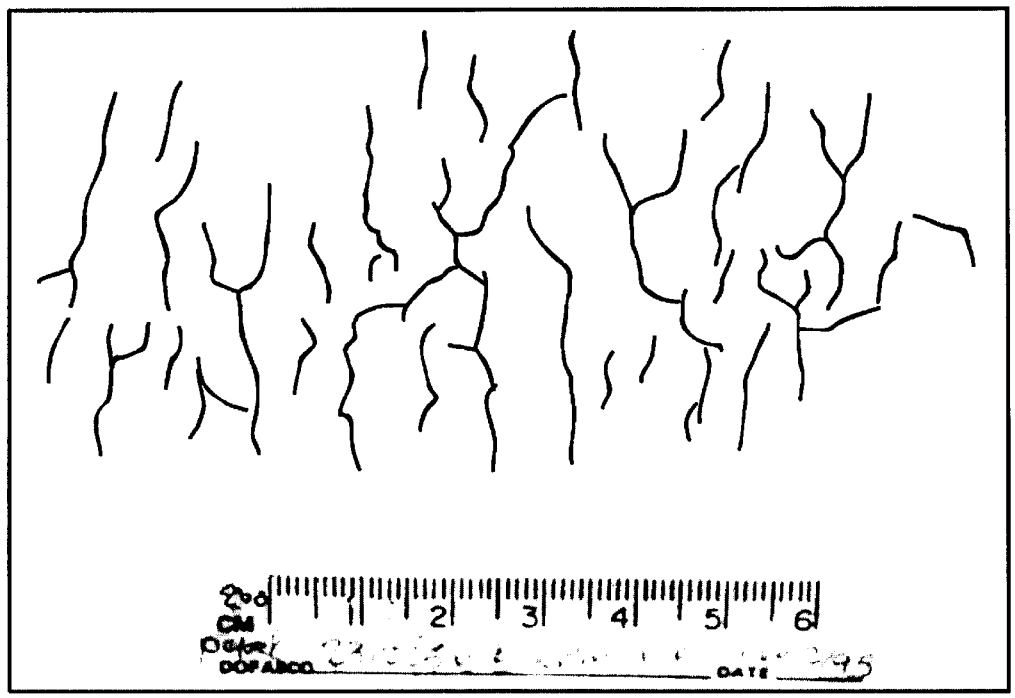
Figure 5B:
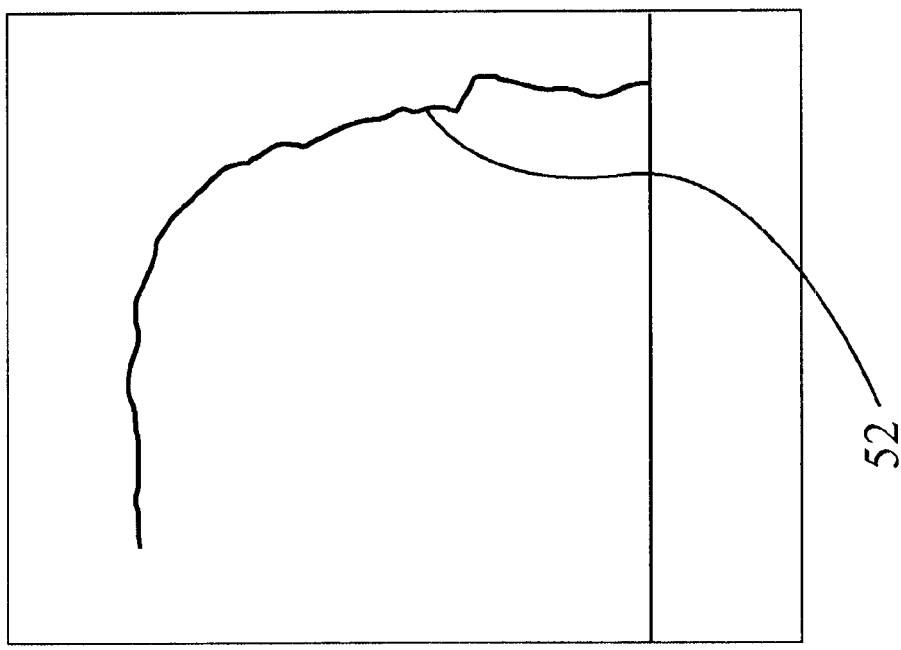
FIG. 5(*a*) is a schematic representation of a photomicrograph showing a thermal crack propagation to the interior of a roll.
Figure 5A:
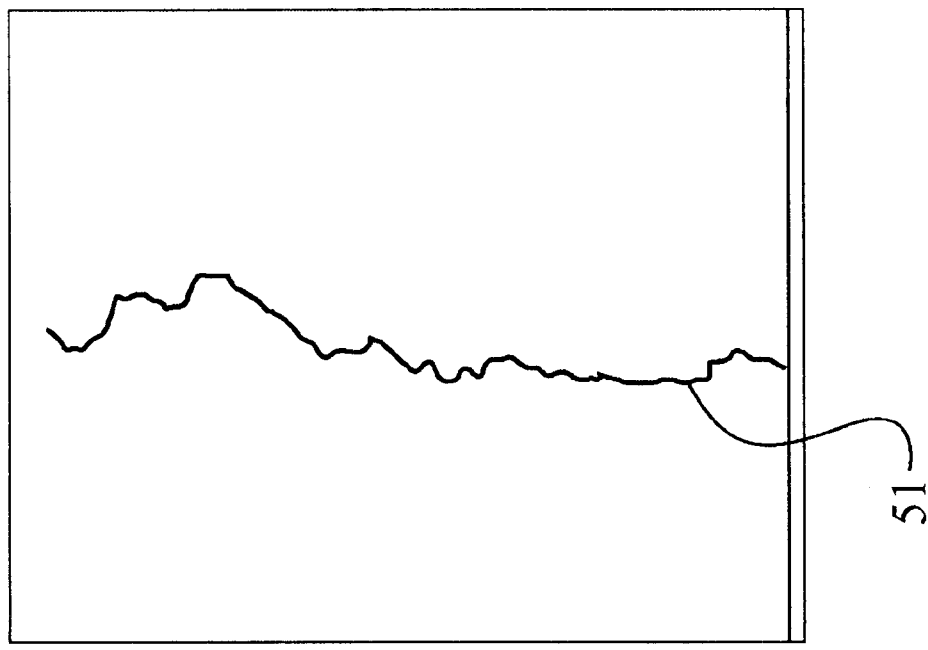

A typical analogue pattern of output voltage signals generated from applying an eddy current voltage to a mill roll having a thermal roll defect is indicated by referenced numeral 41 in FIG. 4 adjacent to the corresponding photomicrograph showing the thermal crack 42.

Figure 6:
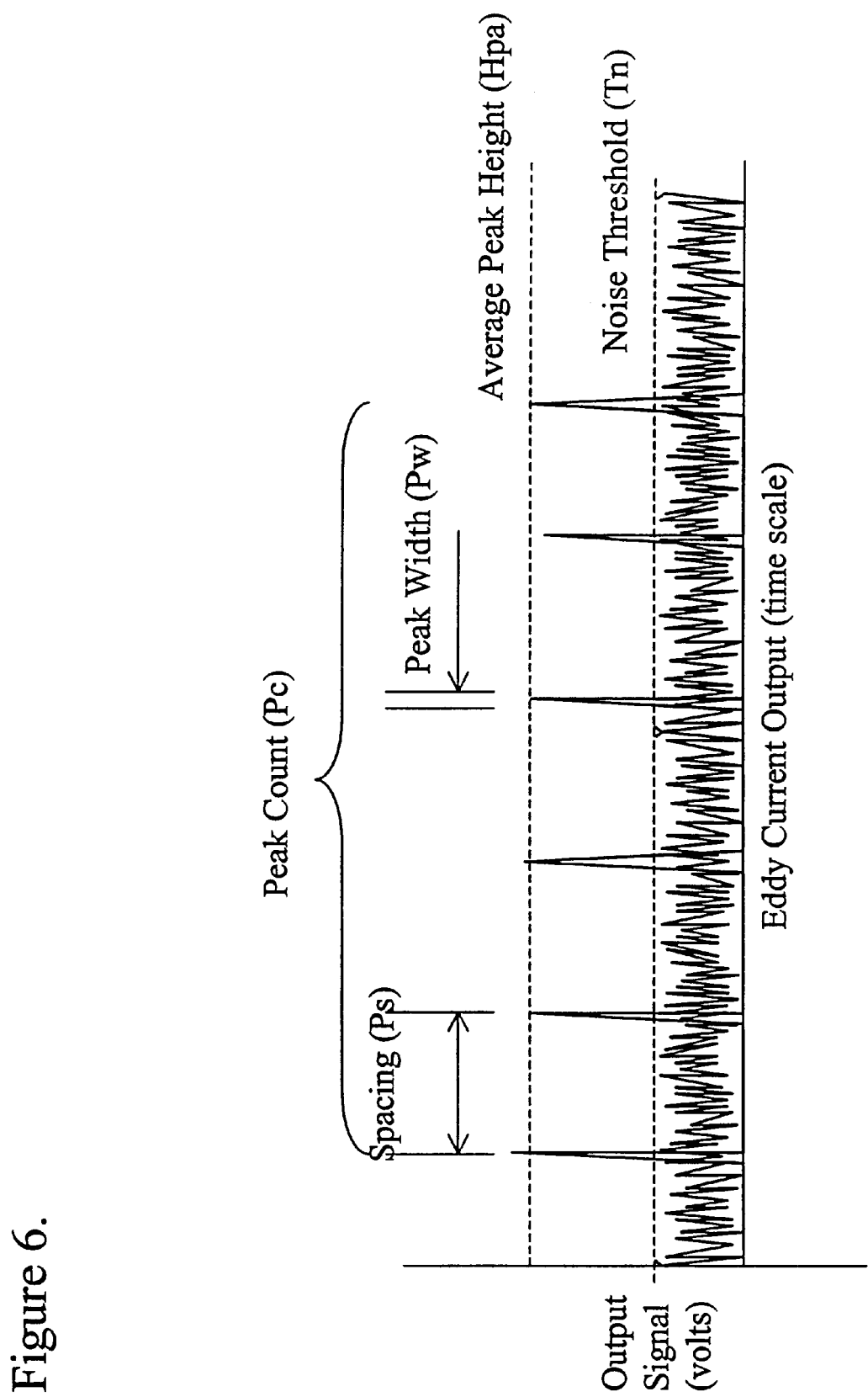
FIG. 6 is a schematic defect map showing a pattern associated with a typical thermal crack.

A simplified version of a thermal crack defect map is shown in FIG. 6. Thermal (firecracks) cracks can be distinguished by noting the repetitive spacing between analogue outputs of the detection system in the following way:

The average peak height Hpa is greater than the noise level Tn by a factor of 3–5 (aka signal to noise ratio).

The peak width Pw can vary between 0.04 and 0.10 seconds (depending on the rotational speed of the roll and travel speed of the sensor).

Peak spacing Ps is equal to the roll circumference C divided by the rotation speed Wr of the roll.

The peak count Pc (number of peaks greater than the noise threshold) is greater than a product width factor N generally corresponding to the width of flat metal being rolled and the travel speed of the inspection transport system.

Thermal Crack Definition

Hpa>K*Tn (K=Signal to noise threshold≈3–5)

Pw=between 0.04 (predetermined time constant $\tau_1$) and 0.10 seconds (predetermined time constant $\tau_2$)

Ps=C/Wr(C=circumference of roll, Wr=speed of roll).

Pc=Σ Peaks>Tn,>C/Wr

As will be seen in FIG. 4, a new thermal crack appears as a series of equally spaced lines in the middle section of the recording and defines a crack defect map. The areas of the plots representing each end of the roll will not be affected. The thickness of the lines should not vary more than one line width and be oriented parallel to the centerline. The previous crack defect map is compared to the present crack map to determine if the cracks are new or old.

Figure 7:
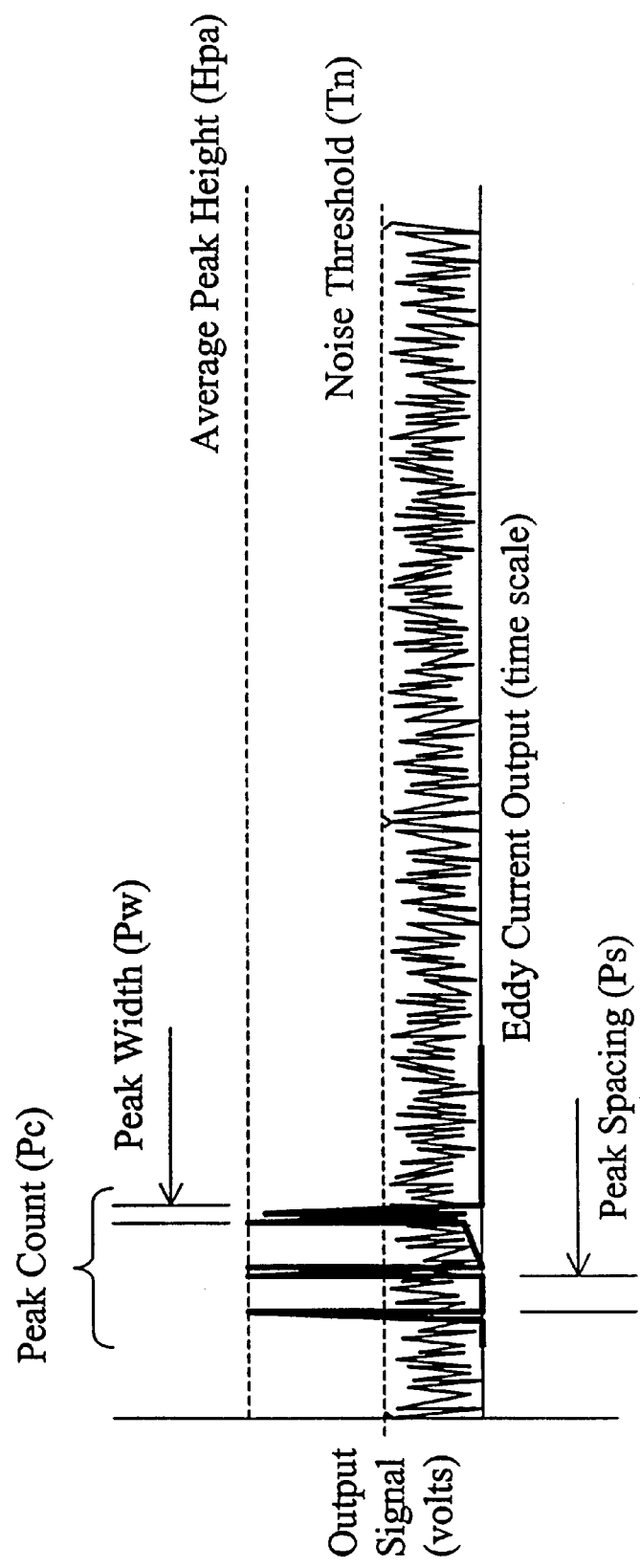
FIG. 7 is a schematic defect map showing a pattern associated with a mechanical impact crack.

A simplified output voltage signal pattern from applying an eddy current voltage to a miii roll having a mechanical impact crack is shown in FIG. 7. The cracks may appear as a single line on a plot or may cover 100% of the roll surface. The pattern is not a series of equally spaced lines and is not restricted to the middle section of the roll. The thickness of the lines may vary more than one line width and the lines are not necessarily oriented parallel to the centerline. Amplitude or severity values will not decrease significantly with additional material removal during successive grinding passes. Ultrasound signals of near surface reflectors at the same location will confirm a pressure crack determination. The previous crack defect map is compared to the present crack map to determine if the cracks are new mechanical or old thermal cracks. The retrieval of past roll inspections will show the areas of old cracking. Any new "non-thermal" areas will be considered mechanical.

Mechanical impact cracks may be distinguished from thermal cracks by noting the configuration of peaks and random peak spacing in contrast to that identified for thermal cracks. The simplified output voltage pattern of FIG. 7 is characterized as follows:

The average peak height Hpa is greater than the noise level by a factor of 3–5 (aka signal to noise ratio).

The peak width Pw is less than 0.04 or greater than 0.10 the maximum time for a thermal crack (The actual value depends on defect size, the rotational speed of the roll and travel speed of the sensor).

Peak spacing Ps is less than the roll circumference C divided by the rotation speed Wr of the roll.

The peak count Pc (peaks greater than the noise threshold) is less than a product width factor N or constant and is generally less than the width of flat metal product being rolled.

Stress Crack Definition

Hpa>K*Tn (K≈3–5)

Pw>0.10 seconds (predetermined time constant $\tau_2$) or Pw<0.04 (predetermined time constant $\tau_1$)

Ps<C/Wr

Pc=Σ Peaks>Tn, <N (N=a minimum number of peaks based on product width)

Figure 8:
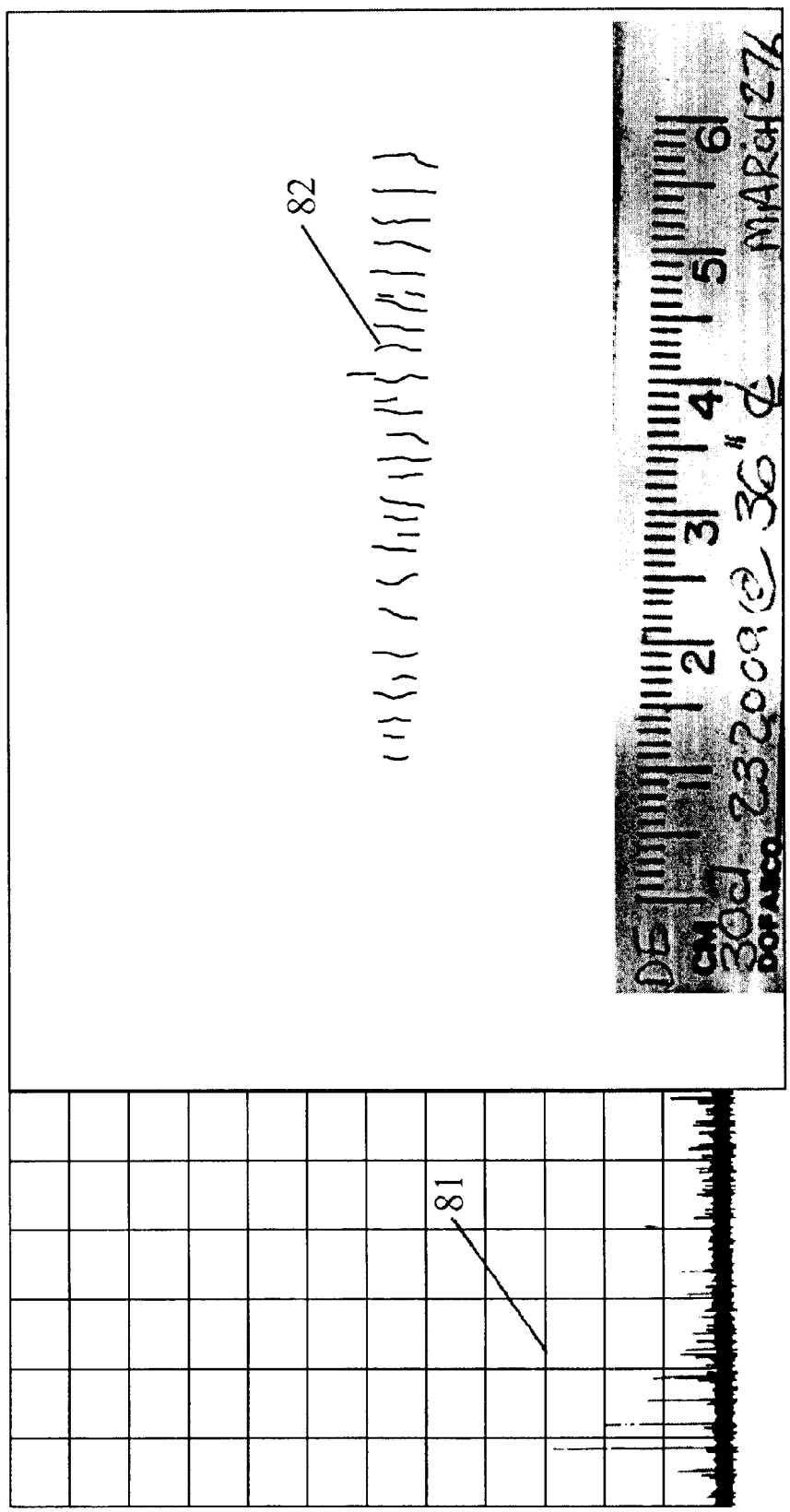
FIG. 8 is a schematic representation of a photomicrograph and associated eddy current voltage plot showing a typical grinding defect at the roll surface.

The appearance of non-thermal roll defects such as grinding defects 82 shown in the photomicrograph of FIG. 8 can vary from a single line to 100% of the roll surface as shown in a typical pattern 81 of output voltage signals generated from applying an eddy current voltage to a mill roll and illustrated by the graphical output of FIG. 8. The pattern 81 is different from a new thermal crack. The previous crack map is compared to the present crack map to determine if the cracks are new mechanical or old thermal cracks.

In the case of metallurgical anomalies the appearance of analog signals plotted on a graph can vary from a single line to 100% of the roll surface. The pattern is similar to a pressure crack. The previous surface inspection crack defect map is compared to the present crack map to determine if the cracks are new anomalies or old thermal cracks. The internal inspection map may show the depth of the anomalies. A surface inspection bruise map may show if the anomalies are associated with any new hardness variations or old.

Acceptance/Rejection Criteria

The goal of the criteria detailed below is to provide rolls without defects that will mark the strip or cause roll failures. Roll defect severity is correlated with surface inspection reports to determine the thermal crack thresholds. Analysis (dimensions and depth) of the defects initiating the roll failures provides the data to determine the internal inspection criteria. The ultrasound inspection of new and used rolls provides the data to determine the internal severity threshold limits.

In a hot strip mill, rolls containing thermal cracks are acceptable to use in early stands (typically 1 to 4), whereas, in cold rolling mills (tandem mills and reversing mills) all types of cracks and surface damage must be removed. At the hot mill, crack severity in the early stands in acceptable ranges does not mark a strip. The allowable severity crack rating decreases with decreasing roll diameter. Rolls with more severe cracks may be used in stand one. Any thermal crack that has an associated near surface internal indication must not be used. Old thermal cracks with pitting greater than 1 mm width along the crack length must be repaired to prevent strip marks. Thermal crack severity decreases with grinding loss. A grinding loss of 0.040" will produce an approximate decrease of 1.0 volts in the signal severity.

All pressure cracks must be removed. Pressure cracks will propagate under fatigue and result in roll failure or spall causing product marring with continued mill use. Their severity does not decrease at the same rate as the thermal crack severity. This type of crack is deeper and does not readily change its pattern compared to the thermal crack.

All grinding defects must be removed. These minor crack defects cause changes in the surface roughness of the roll and transfer to the strip surface.

All metallurgical anomalies must be removed. Metallurgical anomalies such as porosity, non-metallic inclusions and hardness variations mark the strip product from a rolling mill. These defects will appear as pressure crack indications on the surface. Poor shell/core interface quality and defects will lead to roll failures. Ultrasound inspection will detect the near surface, mid-shell and interface anomalies. Internal reflectors of 1.5" width and complete loss of sound transmission through the roll must not be used. Roll failure will result from reflectors with high acoustic impedance. Rolls containing metallurgical anomalies must be held for evaluation and possible claims against the manufacturer for poor quality resulting from flaws created during production of the roll.

Threshold Values

In accordance with the invention, studies are conducted to relate any change in the surface and internal inspection system responses to a change in defect severity. The study produces a relationship between grinding losses and the change in defect severity. Grinding practices and acceptance/rejection criteria are developed to assist an operator in determining the disposition of the roll. Rolls requiring large losses are routed to designated repair grinders.

The eddy current surface inspection system used by applicant produces a one-volt change for every forty thousandths of an inch change in grinding loss. This is a typical relationship for thermal cracks and grinding defects. Pressure crack and surface anomaly severity do not always follow the above relationship.

Figure 9:
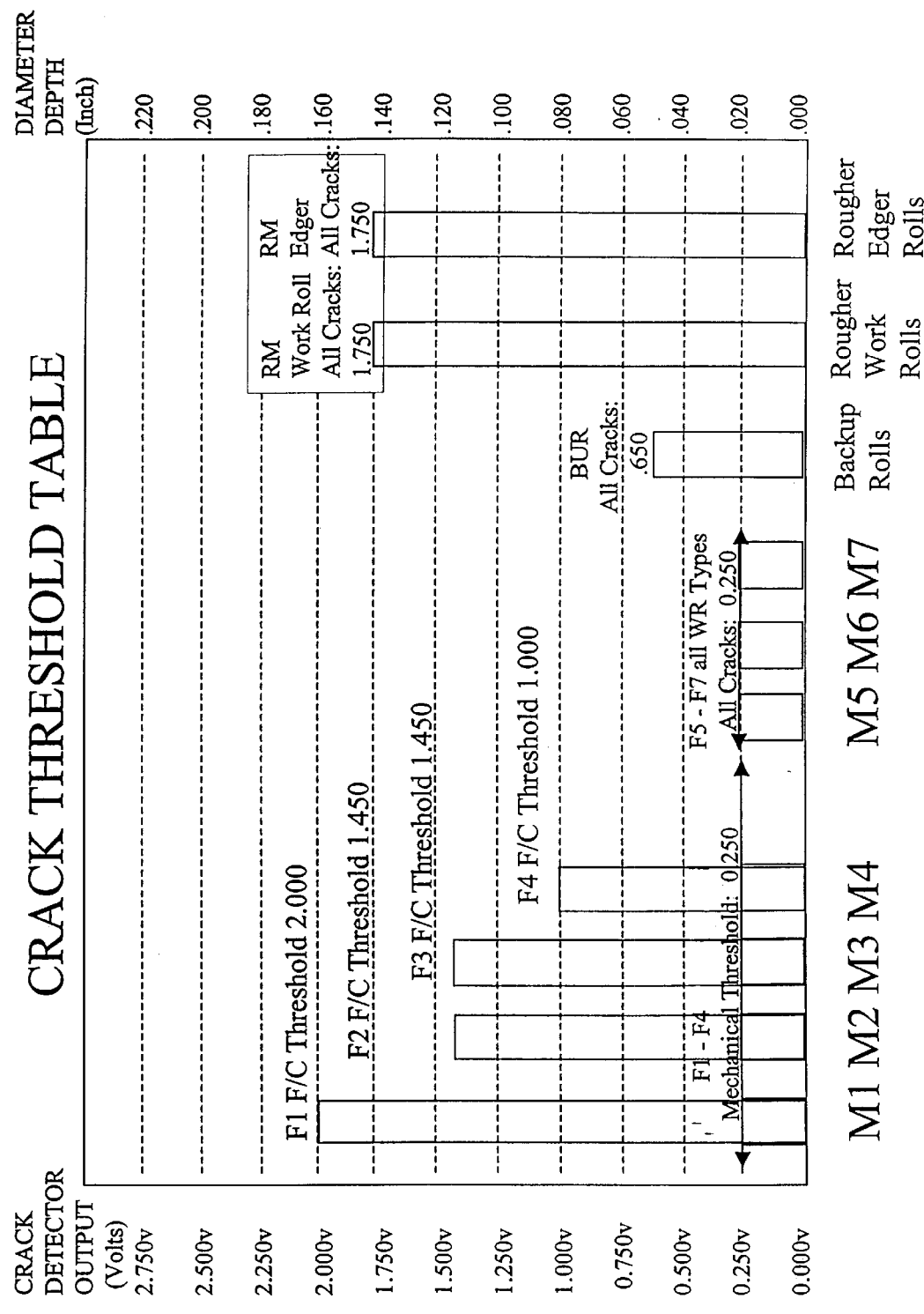
FIG. 9 is a bar chart showing threshold signal values for rolls in mill stands M1 to M7, backup rolls, rough work rolls, and rougher edger rolls.

Typical thresholds applicable to mill rolls for a hot mill (volts/severity) for crack per stand are shown in FIG. 9. Allowable crack severity decreases as the roll moves from tandem mill stand one to four (M1 to M4). Rolls used in stand five to seven (M5 to M7) must be surface defect free and a minimum crack threshold is maintained at a severity of 0.25 volts. Hardness variations of 5 points shore "C" must be detected. This change in hardness will mark the strip.

Internal Indications

An ultrasound flaw detector is calibrated on 5/64" flat bottom hole standards. Distance amplitude correction is required to display the same severity for the same defect size at any depth. The amplitude (Y axes) of signal from a flat bottom hole at the minimum near surface inspection depth is adjusted to maximum reference value ie.80% screen height at 1.5" depth. Test conditions are acceptable if the amplitude of the signal from a flat bottom hole at the maximum inspection depth (deeper than the interface) produces a signal at a screen height equivalent to the reference value divided by the maximum depth/minimum depth ratio ie.40% screen height at 3.0" depth. This setup is for the confirmation of the vertical linearity. Horizontal linearity is set up by adjusting the flaw detector controls to make the depth (X axes) indications appear at the correct distance on the screen. On a five inch range (10 divisions total) the 1.5" depth should appear at the third division from the left. The depth indication from a 3.0" hole should appear at the sixth division.

The threshold is set for detection of reflectors with a diameter 5/128"(1 mm). This is a 40% indication of the possible 100% maximum screen height if calibrated on a 5/64" flat bottom hole.

Threshold is based on severity and size of reflector. Indications exceeding the threshold values for the given depth and a minimum dimension of 1.5" will be rejected. This appears on the video display terminal 9 (FIG. 1) as a 3×3 (0.5" resolution) highlighted matrix. A variable threshold is used to assist the operator to analyze the indications. The maximum indications in the near surface, shell and interface zones must be shown for each unit of surface area resolved on the VDT, 0.5" minimum resolution.

Roll shop operating practices have been developed by applicant in order to document and standardize the testing, interpretation and disposition of mill rolls in the roll grind shop. Various tests can be applied to the roll including eddy current tests for surface cracks, magnetism, variations in microstructure or hardness and voids (also known as round hole defects, spalls, porosity, etc.) The defect type, severity, allowable threshold, reaction and disposition is determined as a result of the test.

Statistical methods can be applied to characterize various crack types including thermal cracks (bar firecracks) and mechanical cracks (stress cracks, localized overload, impacts). While such a characterization was previously limited to crack depth, in accordance with the invention, it is now possible to additionally distinguish between crack types by the analysis of the pattern of detection equipment signal outputs for example the patterns characterized in FIG. 6 and FIG. 7. Once clearly identified, the grinding procedure specified for the crack type can be selected and a minimum amount of material removed to render the roll useful for the rolling operation without risk of catastrophic failure in service.

A crack threshold table (FIG. 9) has been developed by applicant based on the specific knowledge gained from the study of many various roll types and the analysis of many defects found in the mill roll surface through various non-destructive testing techniques. For each mill stand (M1, M2, M3 . . . ), roll type, and specific defect (horizontal axis), the repair amount (vertical axis—total metal to be removed by grinding or lathe cutting) can be identified and automatically executed by a machine computerized numeric control system (CNC) 36 (FIG. 3). The voltage pattern from a final inspection of the roll surface is also compared to the threshold table (FIG. 9) and the roll can be dispositioned for mill use 38, additional grinding, or quarantined 39 for further analysis.

The Table of FIG. 9 is in the form of a bar chart where threshold signal values are displayed so as to correspond to the magnitude of output voltage signals generated by a non-destructive inspection system which are acceptable for a roll having a predetermined roll history and mill history. As will be seen from FIG. 9, the threshold for a thermal crack on a roll in stand M1 is 2.250 volts for an eddy current testing system and is therefore significantly higher than the threshold of 0.250 volts acceptable for mechanical stress induced cracks. Accordingly, the depth of material which needs to be removed during grinding of a roll and shown on the opposing vertical axis to that showing voltage amplitude is correspondingly less for a roll having an output voltage test pattern characteristic of a thermal crack than for a roll where the output voltage test pattern characteristic is associated with a mechanical stress crack.

Automatic Control System for CNC Grind Program Execution

The Automatic Control System 34 (FIG. 3) accepts inputs from various modules and automation level programs and test equipment in order to select a grinder machine roll maintenance program which is automatically downloaded to the grind/lathe CNC system 36 for automatic maintenance and preparation of a mill roll. This is different from current systems designed and installed to date, as grinder/lathe machine programs normally reside in the machine CNC code. In accordance with the invention, the CNC code accepts the selected grind/lathe program from the higher level (e.g. Level 1/2 system) and executes the downloaded program without any operator intervention.

i. Control Data Inputs: Roll History Data 22 and specifications are supplied from a Level 2 (a.k.a. higher level) automation system. Mill History Data 23 including mill induced damage from wrecks is supplied from a process control system. Production schedule information is received from a Level 2/3 control system (depending on control system hierarchy) identifying requirements for the next group of products to be manufactured. Roll specifications are supplied from a Level 1/2 database. Roll inspection data from various detection systems 21 are supplied via CNC/Level 1 inputs. The system will 'self-document' a new roll arriving from manufacture (with a record of 'as-built' internal flaws and/or conditions, shell thickness, material strength), and will also be used as pass/fail acceptance criteria of new roll. The system will accumulate preliminary grind/inspect data on new rolls for this purpose. A summary of control data inputs and a representative example of such inputs are shown in the following Table 1.

TABLE 1

CONTROL DATA INPUTS TO HOST MODULE
Various levels and codes are assignable in each category.

| | | | |
|---|---|---|---|
| Roll Specification | Hardness: 850 Ld | Internal Con. L2 C P | Shell Thick: 80 mm |
| Mill Data | Mill Code: 80 | Max Diam: 900 mm | Min. Diam: 700 mm |
| Roll Data | Roll No. 232123 | Type: HSS C2 | Forged |
| Operating Result | Damage: E01 | Type: Repair | Product: Raised Spall |
| Product Schedule | Sched #: 12–123 | Type: Sp-Light | #1 Surface Required |
| Roll Use Specification | Mill Stand: 01 | Position: T | Shift Control: Fixed |
| Inspection Result | T-Crack: H F/C | S-Crack: Clear | Other: Clear |
| Product Specification | Crown: +.01 mm | Tolerance: +0–.005 | Surface: Ra 2.0 μin |
| Other | Future Req. | | | ii. Control Module Application: Control data inputs such as those shown in Table 1 are processed by the Automatic Control System 34 to select a basic grind module required for preparation of the roll surface (e.g. remove wear profile, remove cracks to base threshold). The basic grind module is subsequently modified based on specifications regarding the specific roll type and its maintenance control plan (e.g. high speed steel rolls type 1 require additional safety grind to prevent cyclic stress induced fatigue). Further modifications to the basic grind module are appended based on the manufacturing requirements of the next production campaign (e.g. the next products require a specified roll crown numeric profile). The final modification to the basic grind module include finish surface preparations (e.g. establish roughness as in mill rolls for cold mill tandem mill stand operations). The complete grind module is then transferred to the CNC System 36 for execution.

iii. Automatic Inspection Level: Roll inspection by automatic and manual methods is time consuming and unnecessary inspections will result in reduced productivity in the roll maintenance shop. However, for selected roll types, extra inspections and special inspections are required to protect against catastrophic failure in service, or causing roll related defects in the product being manufactured. Such data inputs are identified at 31 in FIG. 3. Certain roll types require minimum inspection, depending on the mill stand which is targeted. An automatic inspection level function in the host program will assess roll type, mill stand, and product features and specify the required inspection functions to be initiated by the CNC controls at the grinder/lathe e.g. wear test, preliminary (fast) defect inspection, current shape test, final shape test, final defect inspection, internal defect inspection, and/or other required inspections. The inspection test sequence and level is added to the grind module and downloaded to the CNC system 36 for execution.

iv. Intelligent Outputs: An intelligent output includes all typical and common elements of various CNC control programs for grinders and lathes. In roll grinders, these are commonly resident within the CNC control system 36 and must be operator selected and modified to suit the specific roll and its next application. Also, the results of the tests for roll defects and shape must be interpreted and then the CNC program must be modified. All of these actions are managed by the Automatic Control System 34.

v. Example of Final Grind Program: An example of an output from the Automatic Control System 36 will include:

Short Stroke (SS)—10 passes per side (0.20 mm) to remove measured wear profile

Regular Grind (RG)—10–20 full passes (0.20 mm) to remove residual Firecracks to required threshold for this roll and next application.

Safety Grind (SG)—5 full passes (0.01 mm) to remove residual stress, residual cracks from previous campaigns and/or roll specific safety margin specified.

Control Grind (CG)—Full passes as required to meet roll profile specification.

Finish Grind (FG)—5 full low current passes to control shape, taper and eccentricity to required specification.

Final Grind (Super Finish Grind/Sparking Out, SFG)—Full passes as required to control roughness, roll grind mark control.

The above can be summarized as in Table 2, which can be converted by the host system to CNC code which can be interpreted by the CNC System 36. (Note above does not include subroutines for inspection which are coded in a similar manner.)

TABLE 2

EXAMPLE OF HOST MACHINE CONTROL CODE OUTPUT

| CNC Module | Number of Passes | Total Metal Removal | Specification |
|---|---|---|---|
| SS | 10 | 0.20 | 0.0 |
| RG | 10 | 0.20 | 0.0 |
| SG | 5 | 0.01 | 0.0 |
| CG | 0 | 0 | –.001 |
| FG | 5 | 0 | –.001 |
| SFG | 5 | 0 | –.001 |

Test Roll Design

Figure 10:
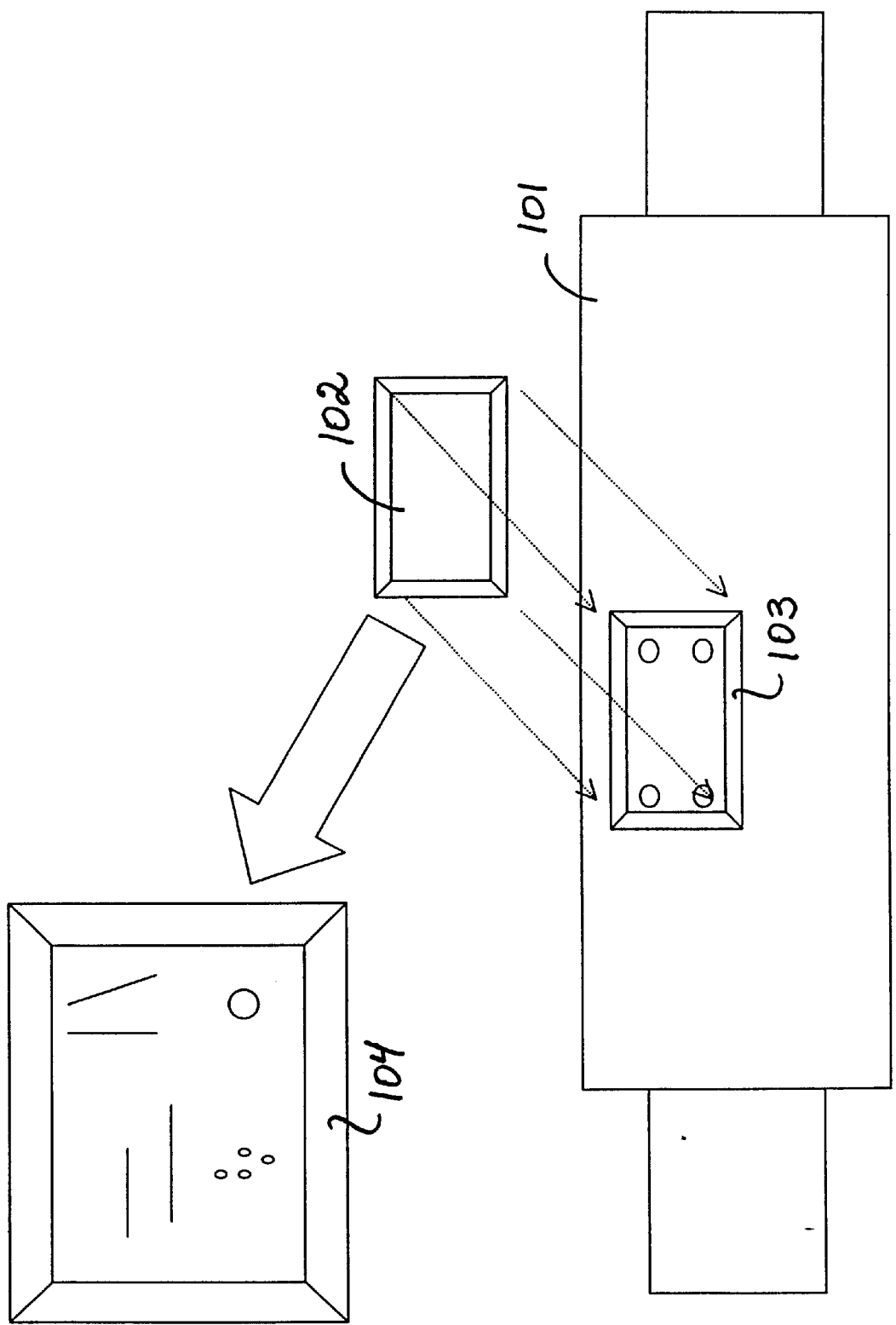
FIG. 10 is a schematic exploded view showing a mill roll insert with manufactured defects and forming part of a test roll for calibration of nondestructive testing equipment.

A test roll 101 (shown in FIG. 10) is provided to allow calibration and reliability testing of the roll testing equipment 21 (e.g. Eddy Current, Ultrasonic, etc). The test roll 101 has a cavity 103 for receiving a specially designed insert 102 of the appropriate material that can be installed and removed from a common roll in use at various manufacturing sites. The insert 102 has precision manufactured "defects" 104 comprising line and void anomalies machined into surface and subsurface locations. These manufactured defects 104 are factory calibrated and certified as test standards. The insert 102 contains various line cracks, at various depths and configurations. Also, round hole defects are machined at various depths and in clusters. The test roll 101 is used on site at the grinder or lathe or other roll maintenance equipment for the quick and accurate calibration of measurement and testing equipment.

It will be understood that several variations may be made to the above-described preferred embodiment of the invention, as will be appreciated by those skilled in the art.

What is claimed is:

1. A method for inspecting a mill roll used for producing flat rolled metal strip and for disposition of a mill roll of predetermined type and in service on a predetermined mill stand as a function of defect classification of any defects detected in said mill roll, the method comprising the steps of:
    a) applying a nondestructive inspection system to generate variable amplitude output voltage signals corresponding to changes in physical properties along a reference direction for at least a portion of the mill roll, any said changes in physical properties corresponding to a mill roll defect;
    b) defining an output voltage signal pattern from said variable amplitude output voltage signals;
    c) classifying said mill roll defect in accordance with predetermined patterns of output voltage signals to assign a defect classification;
    d) selecting a threshold signal value corresponding to said defect classification for the type of mill roll being inspected on said mill stand;
    e) calculating a difference between a maximum peak height for the output voltage signals and said threshold signal value; and
    f) defining corrective action for disposition of the mill roll in accordance with said calculated difference.

2. Method according to claim 1 in which said output voltage signal pattern is a graphical display of said output voltage signals as a function of location on said roll in said reference direction.

3. Method according to claim 1 in which said inspection system generates signals corresponding to changes in physical properties which are selected from the group comprising magnetic permeability, electrical conductivity, and acoustic impedance.

4. Method according to claim 1 in which the corrective action is selected from the following:
    a) removing a depth of material from the mill roll, said depth being a function of said calculated difference between the maximum peak height for the output voltage signals and said threshold signal value;
    b) reclassifying the roll for continuing service as a mill roll on a different mill stand; and
    c) scrapping the mill roll to discontinue service.

5. Method according to claim 1 in which said defect classification is selected from the group comprising:
    mechanical roll defects and thermal roll defects.

6. Method according to claim 5 in which a threshold signal value for a thermal roll defect is greater than for a mechanical roll defect and a smaller depth of material is removed to correct a thermal roll defect than to correct a mechanical roll defect.

7. Method according to claim 1 in which the reference direction is a straight line parallel to a mill roll longitudinal axis.

8. Method according to claim 1 in which steps a, e, and f are repeated, as necessary, and a depth of material is removed from the roll mill until any output voltage signals generated in step a) are less than said threshold signal value selected in step d).

9. A method for inspecting a mill roll used for producing flat rolled metal strip and for disposition of a mill roll of predetermined type and in service on a predetermined mill stand as a function of defect classification of any defects detected in said mill roll, the method comprising the steps of:
    a) applying an eddy current voltage to generate variable amplitude eddy current voltage signals corresponding to any changes in electrical conductivity along a reference direction for at least a portion of the mill roll, any said changes in electrical conductivity corresponding to a mill roll defect;
    b) defining an output voltage signal pattern from said variable amplitude eddy current voltage signals;
    c) classifying said mill roll defect in accordance with predetermined patterns of eddy current voltage signals to assign a defect classification;
    d) selecting a threshold signal value corresponding to said defect classification for the type of mill roll being inspected on said mill stand;
    e) calculating a difference between a maximum peak height for the eddy current voltage signals and said threshold signal value; and
    f) defining corrective action for disposition of the mill roll in accordance with said calculated difference.

10. Method according to claim 9 in which said output voltage signal pattern is a graphical display of said eddy current voltage signals as a function of location in said reference direction.

11. Method according to claim 9 in which the corrective action is selected from the following:
    a) removing a depth of material from the mill roll, said depth being a function of said calculated difference between a maximum peak height for the eddy current voltage signals and said threshold signal value;
    b) reclassifying the roll for continuing service as a mill roll on a different mill stand; and
    c) scrapping the mill roll to discontinue service.

12. Method according to claim 9 in which said defect classification is selected from the group comprising:
    mechanical roll defects and thermal roll defects.

13. Method according to claim 12 in which a threshold signal value for a thermal roll defect is greater than for a mechanical roll defect and a smaller depth of material is removed to correct a thermal roll defect than to correct a mechanical roll defect.

14. Method according to claim 9 in which the reference direction is a straight line parallel to a mill roll longitudinal axis.

15. Method according to claim 9 in which steps a, e, and f are repeated, as necessary, and a depth of material is removed from the mill roll until any eddy current voltage signals generated in step a) are less than said threshold signal value selected in step d).

16. Method according to claim 9 in which a mechanical roll defect classification is assigned for a mill roll having a predetermined roll circumference being rotated at a predetermined rotation speed during said application of the eddy current voltage, where said eddy current voltage signals have a pattern comprising a small series of signals of varying peak width greater than a predetermined time constant $\tau_2$ but less than a predetermined time constant $\tau_1$ and in which peak spacing is less than the roll circumference divided by the rotation speed of the mill roll and the number of peaks is less than a product width factor.

17. Method according to claim 9 in which a thermal roll defect classification is assigned for a mill roll having a predetermined roll circumference being rotated at a predetermined rotation speed during said application of the eddy current voltage detector, where said eddy current voltage signals have a pattern comprising a large series of equally spaced signals of varying peak width less than a predetermined time constant $\tau_2$ but greater than a predetermined time constant $\tau_1$ and in which peak spacing is equal to the roll circumference divided by the rotation speed of the roll and the number of peaks exceeds a product width factor.

18. A system for inspecting mill rolls used in the production of flat rolled metal strip and for defining corrective action for disposition of mill rolls, the system comprising:
   a) data input means for receiving data defining a roll history and mill history associated with a roll being inspected;
   b) a database of threshold signal values each corresponding to an acceptable output voltage signal for a roll having a predetermined roll history and mill history and having a predetermined type of mill roll defect;
   c) a non destructive inspection system for generating variable amplitude output voltage signals corresponding to changes in physical properties associated with mill roll defects;
   d) signal processing means for receiving said variable amplitude output voltage signals and defining a voltage signal pattern;
   e) signal classification means for classifying said voltage signal pattern in accordance with predetermined patterns of output voltage signals associated with predetermined defect classifications each having a predetermined threshold signal value;
   f) computation means to calculate a difference in a maximum peak height for the output voltage signals characterizing said voltage signal pattern and said predetermined threshold signal value and to define corrective action for disposition of the mill roll; and
   g) transfer means for conveying information about said corrective action.

19. System according to claim 18 in which the roll history includes data defining roll size, roll speed, roll material and roll construction type, and a roll identification tag.

20. System according to claim 18 in which the mill history includes data defining a mill stand, a mill operating temperature, a mill output product tag, a mill incident report, and a roll identification tag.

21. System according to claim 20 in which the mill output product tag includes data defining product width, product gauge, and product chemistry.

22. System according to claim 18 in which the non-destructive inspection system includes an eddy current probe sensor.

23. System according to claim 18 in which the non-destructive inspection system includes an ultrasonic probe sensor.

24. System according to claim 18 in which the signal processing means includes a mill roll defect plotting programme and graphical display means for displaying said voltage signal pattern.

25. System according to claim 18 in which said transfer means is a visual display coupled to said computation means.

26. System according to claim 18 coupled to a mill roll grinding apparatus for removing a predetermined depth of material from a mill roll, said depth being a function of said calculated difference between the maximum peak height for the output voltage signals and said threshold signal value.

27. A method for inspecting a mill roll used for producing flat rolled metal strip and for disposition of a mill roll a predetermined type and in service on a predetermined mill stand as a function of defect classification of any defects detected in said mill roll, the method comprising the steps of:
   a) applying a nondestructive inspection system to generate variable amplitude output voltage signals corresponding to changes in physical properties along a reference direction for at least a portion of the mill roll, any said changes in physical properties corresponding to a mill roll defect;
   b) defining an output voltage signal pattern from said variable amplitude output voltage signals;
   c) classifying said mill roll defect in accordance with predetermined patterns of output voltage signals to assign a defect classification selected from the group comprising mechanical roll defects and thermal roll defects;
   d) selecting a threshold signal value corresponding to said defect classification for the type of mill roll being inspected on said mill stand said threshold signal value being greater for a thermal roll defect than for a mechanical roll defect;
   e) calculating a difference between a maximum peak height for the output voltage signals and said threshold signal value; and
   f) defining corrective action for disposition of the mill roll in accordance with said calculated difference, a smaller depth of material to be removed to correct a thermal roll defect than to correct a mechanical roll defect.

28. A method for inspecting a mill roll used for producing flat rolled metal strip and for disposition of a mill roll of predetermined type and in service on a predetermined mill stand as a function of defect classification of any defects detected in said mill roll, the method comprising the steps of:
   a) applying an eddy current voltage to generate variable amplitude eddy current voltage signals corresponding to any changes in electrical conductivity along a reference direction for at least a portion of the mill roll, any said changes in electrical conductivity corresponding to a mill roll defect;
   b) defining an output voltage signal pattern from said variable amplitude eddy current voltage signals;
   c) classifying said mill roll defect in accordance with predetermined patterns of eddy current voltage signals to assign a defect classification selected from the group comprising mechanical roll defects and thermal roll defects;
   d) selecting a threshold signal value corresponding to said defect classification for the type of mill roll being inspected on said mill stand said threshold signal value being greater for a thermal roll defect than for a mechanical roll defect;
   e) calculating a difference between a maximum peak height for the eddy current voltage signals and said threshold signal value; and
   f) defining corrective action for disposition of the mill roll in accordance with said calculated difference a smaller depth of material to be removed to correct a thermal roll defect than to correct a mechanical roll defect.

29. Method according to claim 28 in which a mechanical roll defect classification is assigned for a mill roll having a predetermined roll circumference being rotated at a predetermined rotation speed during said application of the eddy current voltage detector, where said eddy current voltage signals have a pattern comprising a small series of signals of varying peak width greater than a predetermined time constant $\tau_2$ but less than a predetermined time constant $\tau_1$ and in which peak spacing is less than the roll circumference divided by the rotation speed of the mill roll and the number of peaks is less than a product width factor.

30. Method according to claim 28 in which a thermal roll defect classification is assigned for a mill roll having a predetermined roll circumference being rotated at a predetermined rotation speed during said application of the eddy current voltage detector, where said eddy current voltage signals have a pattern comprising a large series of equally spaced signals of varying peak width less than a predetermined time constant $\tau_2$ but greater than a predetermined time constant $\tau_1$ and in which peak spacing is equal to the roll circumference divided by the rotation speed of the roll and the number of peaks exceeds a product width factor.

* * * * *